United States Patent [19]

Timm et al.

[11] Patent Number: 4,474,187
[45] Date of Patent: Oct. 2, 1984

[54] THRESHOLD PENILE RIGIDITY MEASURING DEVICE

[75] Inventors: Gerald W. Timm, Minneapolis, Minn.; William E. Bradley, Huntington Beach, Calif.

[73] Assignee: Dacomed Corporation, Minneapolis, Minn.

[21] Appl. No.: 378,709

[22] Filed: May 17, 1982

Related U.S. Application Data

[63] Continuation-in-part of Ser. No. 318,373, Nov. 5, 1981.

[51] Int. Cl.³ .............................................. A61B 5/10
[52] U.S. Cl. .................................. 128/774; 128/694; 33/174 D
[58] Field of Search ........... 128/774, 782, 694, 138 R; 33/174 D, 179, DIG. 13

[56] References Cited

U.S. PATENT DOCUMENTS

| 3,572,091 | 3/1971 | McFarland . |
| 3,820,529 | 6/1974 | Gause et al. . |
| 4,103,678 | 8/1978 | Karacan et al. . |
| 4,258,720 | 3/1981 | Flowers . |

OTHER PUBLICATIONS

"A Simple and Inexpensive Transducer for Quantitative Measurements of Penile Erection During Sleep", *Behavior Research Methods and Instrumentation*, vol. 1, pp. 251–252, 1979, Author: Ismet Karacan.
"Some Characteristics of Nocturnal Penile Tumescence in Young Adults", *Archives General Psychiatry*, vol. 26, pp. 351–356, 1972, Author: Ismet Karacan.
"Sleep Related Penile Tumescence as a Function of Age", *American Journal of Psychiatry*, vol. 132, pp. 932–937, Sep., 1975, Author: Ismet Karacan.
"Nocturnal Penile Tumescence Monitoring with Stamps", *Urology*, vol. 15, pp. 171–172, 1980, Authors: John M. Barry, M.D., Bruce Blank, M.D., and Michael Boileau, M.D.
"Normative Studies on a New Device for Evaluation for Nocturnal Penile Tumescence", Notice of American Urological Association, Inc., 77th Annual Meeting, Presented by Dr. Alvaro Morales.
Brochure for Erectiometer, Manufacturer: Walter Koss OHG.

*Primary Examiner*—Lee S. Cohen
*Assistant Examiner*—John C. Hanley
*Attorney, Agent, or Firm*—Merchant, Gould, Smith, Edell, Welter & Schmidt

[57] ABSTRACT

An apparatus (10) for measuring a predetermined penile rigidity or hardness in a penile tumescent event. The apparatus (10) includes a band-like structure (12) for releasably engaging a penis (11). Suitably attached and associated with band-like structure (12) are releasable fasteners (15) for detecting a predetermined force in a penile tumescent event whereby penile rigidity or hardness can be measured.

6 Claims, 15 Drawing Figures

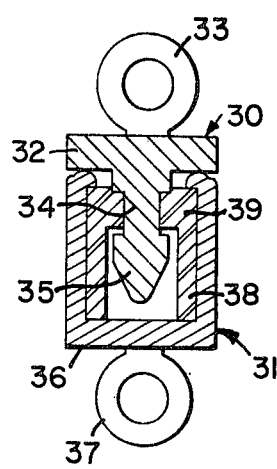
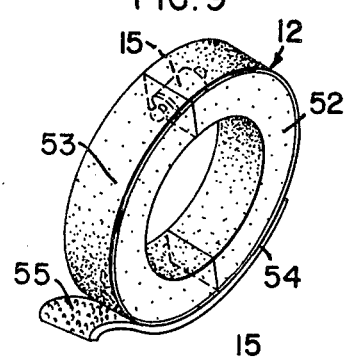
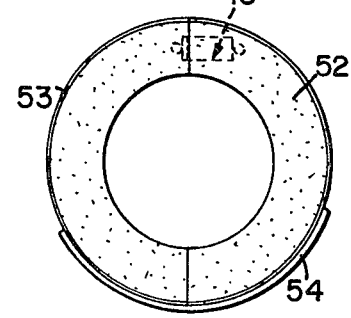
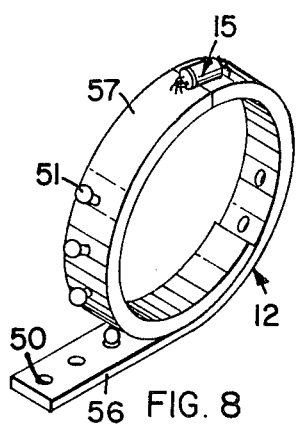

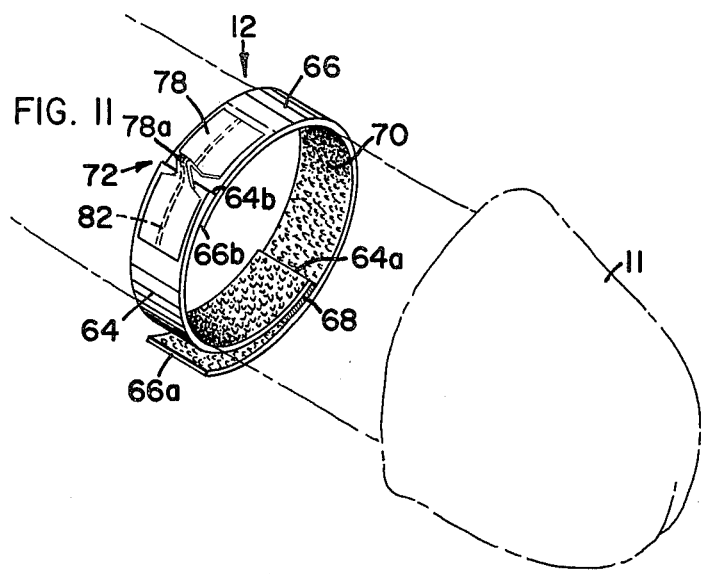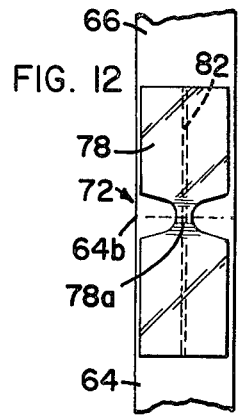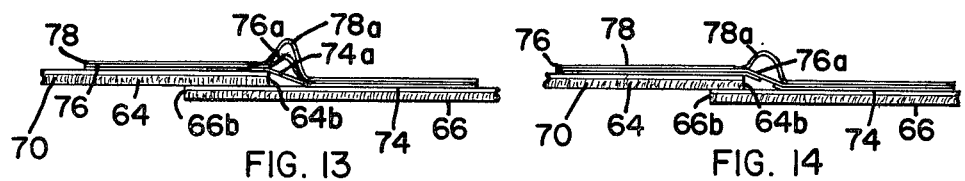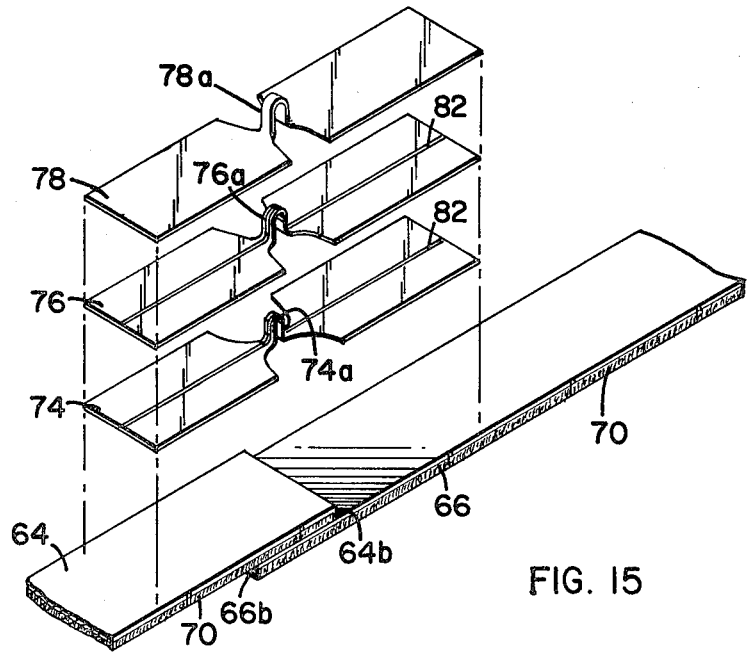

THRESHOLD PENILE RIGIDITY MEASURING DEVICE

This application is a continuation in Part of Ser. No. 318,373 filed Nov. 5, 1981 pending.

TECHNICAL FIELD

The present invention relates to an apparatus for detecting a predetermined force or penile hardness during a penile tumescent event.

BACKGROUND OF THE INVENTION

Studies have shown that men with psychogenic impotence generally have normal sleep erections, whereas men with organic impotence have sleep erections that correspond to their impaired wake performance. Such studies have alerted the scientific community of the potential usefulness of nocturnal penile tumescent monitoring in the differential diagnosis of sexual impotence. As a result of the recognition that nocturnal penile tumescent monitoring can be of assistance in diagnosing male erectile impotence, various types of devices and techniques for conducting such monitoring have been developed.

In an article entitled "A Simple and Inexpensive Transducer for Quantitative Measurement of Penile Erection During Sleep", Behavior Research Methods and Instrumentation, Volume 1, pages 251–252, 1969, Ismet Karacan describes a mercury strain-gauge transducer for detecting penile erection. The transducer device is an elastomeric mercury filled tube which is suitably connected to a wheatstone bridge and amplifier circuit for recording purposes. As the transducer changes size during penile erection, its electrical resistance changes thereby causing the amplified output from the wheatstone bridge to change. The amplified changes in the output are recorded enabling penile activity to be recorded.

In an article entitled "Some Characteristics of Nocturnal Penile Tumescence in Young Adults", Archives General Psychiatry, Volume 26, pages 351–356, 1972, Ismet Karacan et al. describes the normative characteristics of nocturnal penile tumescence (NPT) in a group of 20 to 26 year old men who were measured during continuous all-night recording utilizing the mercury strain-gauge transducer.

Additionally, a number of devices and procedures for monitoring penile tumescence during sleep are noted and referenced in an article entitled "Sleep Related Penile Tumescence as a Function of Age", American Journal of Psychiatry, Volume 132, page 9, Sept. 1975.

In U.S. Pat. No. 4,103,678 issued to Ismet Karacan et al. an apparatus is disclosed for recording minute variations in mercury strain-gauge transducers positioned at the base and the tip of the penis.

The above-referenced materials relate to nocturnal penile tumescence activity and not to the measurement of penile rigidity or hardness during the tumescent event. While it is recognized that nocturnal penile tumescence activity is important to the evaluation of organic impotence, another significant aspect in evaluating organic impotence is the quality or rigidity/hardness achieved during the penile tumescent event.

The mercury strain-gauges described by Ismet Karacan can provide a measurement of the changes in penile size during a penile tumescent event by changing their impedance as they expand and contract with variations in the penis circumference. The mercury strain-gauges do not, however, provide for measurement of penile rigidity or hardness since the strain-gauges are very elastomeric. A very slight amount of force will fully expand the strain-gauges just as would a larger amount of force.

In addition, the mercury strain-gauge necessitates a rather elaborate monitoring mechanism. The monitoring normally must occur in a health care facility under the supervision of trained experts. This requires that the patient may be in the health care facility overnight and be subjected to fairly elaborate testing. In addition to creating a substantial imposition on the patient's daily routine, substantial expense is associated with the support facilities and support personnel required to obtain valid test results.

In an article entitled "Nocturnal Penile Tumescence Monitoring with Stamps", Urology, Volume 15, pages 171–172, 1980, a stamp technique is described for detecting complete nocturnal erection for the evaluation of impotence. In this technique, a strip of four postage-type stamps is wrapped snuggly around the penis, and the overlapping stamp is moistened to provide a one half to one stamp overlapping seal. The nocturnal penile tumescent stamps, each one and one quarter by one inch, are made on ten by eight inch sheets of paper having water base glue on the opposite side. The patients or subjects are able to perform the evaluations at home rather than go to the hospital, resulting in substantial financial savings. The article indicated that three nights of inhospital nocturnal penile tumescence testing including direct observation of indicated erections and physicians professional fee, currently cost roughly $500. The stamp testing method costs 30 cents for three nights of outpatient testing.

While the stamp testing method attempts to measure penile rigidity or hardness during a penile tumescent event rather than penile activity, the stamp testing technique does not provide desired accuracy and reproducability. The stamps have a tendency to release after being wetted and stuck together. In addition, the force required to break the perforations between adjacent stamps varies substantially. Thus, the above described stamp technique does not provide a method for accurately detecting a predetermined penile rigidity or hardness.

The present invention offers a safe, simple, accurate and reproducible test which can be used at home and provides a very effective tool in the evaluation of impotence.

SUMMARY OF THE INVENTION

The present invention relates to an apparatus for measuring a predetermined penile rigidity or hardness in a penile tumescent event. The present invention includes means for releasably engaging a penis and associated means for detecting a predetermined force in the penile tumescent event.

In one embodiment of the present invention, the apparatus includes first and second elongated strips of material which are releasably interconnected to form an adjustable length band-like structure. The adjustable length band-like structure transfers the radial pressure exerted by the penis during a penile tumescent event into a generally linear force roughly tangential to the surface of the band-like structure. The first and second elongated strips of material are releasably interconnected at a first end thereof by a hook-like and loop-like releasable self-gripping fastening material such as Velcro. (Velcro is a registered trademark of the Talon Company.)

The first and second elongated strips of material are releasably interconnected at a second end by a fastener or snap-like device which releases upon application of a predetermined force. The snap-like device in one preferred embodiment is a linear coupling that locks when a metal penetrator is pushed into a variable hardness neoprene collar and unlocks or releases when the metal penetrator is pulled out. The penetrator is pulled out of the center of the flexible neoprene collar upon application of a predetermined force. The amount of predetermined force required to release the snap-like device is preset by adjusting the flex characteristics of the neoprene collar.

In another preferred embodiment, an elastic retainer such as a piece of elastic thread is interconnected between the first and second elongated strips of material to prevent the loss of the apparatus from the penis after the snap-like device releases.

The present invention enables the detection of penile rigidity or hardness during a penile tumescent event. This type of measurement is not possible with the mercury strain-gauge transducer which merely measures changes in penis size during a penile erection and does not provide any means for measuring the hardness or rigidity of the penis.

In addition, the present invention in its simplest form requires no supporting equipment, special facilities or support personnel. Thus, the present invention provides a simple but effective and accurate technique for detecting penile rigidity or hardness during a penile tumescent event which may be performed while a person is sleeping at home. Because of its simplicity, the subject or patient is not required to take part in inhospital nocturnal penile tumescence testing thereby avoiding substantial cost. In addition, the testing or screening can be performed with very little impact on a person's daily routine or schedule by not requiring the subject to stay overnight in a health care facility. Since there is no tape or other attachments to the body, there is no discomfort to the subject, thereby allowing the subject to attain a restful night's sleep while the testing is performed.

While the stamp testing technique provides a method for detecting a penile tumescent event, the stamp technique is not nearly as accurate or reproducible as the present invention. The perforated stamps have a tendency to break or separate over a broader range force than the snap-like devices utilized in one embodiment of the present invention. In addition, the snap devices of the present invention can be varied or preset before use to release at varying incremental levels of predetermined force.

The hook-like and loop-like fabric of the present invention requires a very light pressing force to engage the hook-like material to the loop-like material so as to releasably attach the apparatus to the penis. However, the fabric will remain fastened in the presence of substantial linear forces generally tangential to the surface of the band-like structure. The stamp technique requires that the glue on the backing be wetted and that then the stamp be overlayed so as to form a ring-like structure. The connection formed by the glue on the backing of the stamp is not always reliable and has a tendency to give way. In addition, the stamps cannot be reused should they tear or the glue give way. The present invention, however, is easily refastened should it become accidentally dislodged during placement on the penis or at anytime during the testing period.

In still yet another preferred embodiment of the present invention, multiple fasteners can be utilized with the band-like structure. Each fastener device may be releasable at a different predetermined force level thereby providing detection of a plurality of different predetermined forces or levels of penile rigidity or hardness during a penile tumescent event. The stamp technique described above cannot be adjusted predictably in this manner. With the ability to detect a range of predetermined forces, the presence or absence of penile tumescent activity can be detected, and if present, the adequacy of penile erection for vaginal penetration can be assessed.

The present invention is adaptable for use with detection devices having suitable recording instruments capable of recording continuously the magnitude of penile rigidity or hardness during a penile tumescent event. Such a recording instrument might consist of a strip chart recording device similar to that revealed in U.S. Pat. No. 4,103,670. Such devices would be capable of providing a continuous recording of the force levels during a penile tumescent event. Continuous analog or digital monitoring in addition to determining the penile rigidity or hardness during a penile tumescent event would be able to detect each event and count the number of events over a given period of time.

These and various other advantages and features of novelty which characterize the invention are pointed out with particularity in the claims annexed hereto and forming a part hereof. However, for a better understanding of the invention, its advantages, and objects obtained by its use, reference should be had to the drawings which form a further part hereof, and to the accompanying descriptive matter, in which there is illustrated and described a perferred embodiment of the invention.

BRIEF DESCRIPTION OF THE DRAWINGS

In the drawings, in which like reference numerals and letters indicate corresponding parts throughout the several views.

FIG. 7 is a cross-sectional side elevational view of a linear coupling fastener device;

FIG. 8 is a view in perspective of an alternative embodiment of the band-like structure;

FIG. 9 is a perspective view of an alternative embodiment of the band-like structure utilizing two strips of foam-like material suitably interconnected;

FIG. 10 is an elevational view of the alternative embodiment of FIG. 9 with the fastener devices imbedded in the foam-like strips;

FIG. 11 is a view in perspective of yet another embodiment of the present invention;

FIG. 12 is a top plan view of the embodiment illustrated in FIG. 11;

FIG. 13 is a fragmentary side elevational view of the embodiment illustrated in FIG. 11 with all snap elements connected;

FIG. 14 is a fragmentary elevational view of the embodiment illustrated in FIG. 11 with one of snap elements in a released or detection state; and FIG. 15 is an exploded fragmentary view of the embodiment illustrated in FIG. 11.

DETAILED DESCRIPTION OF THE INVENTION

Figure 1:
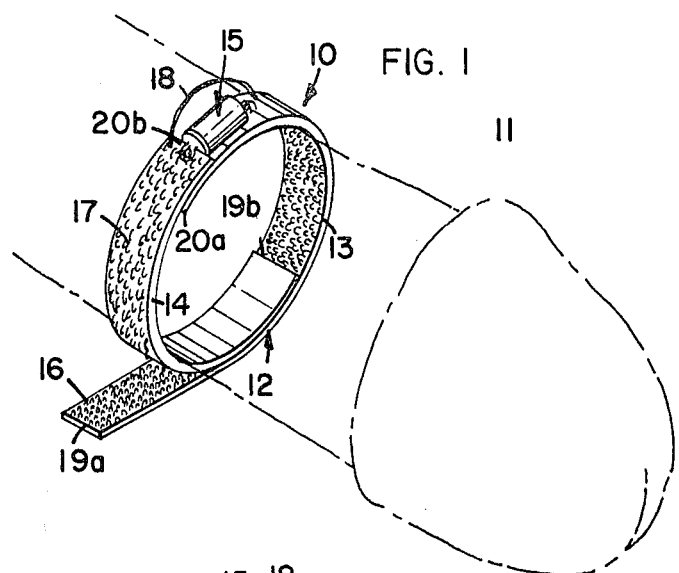
FIG. 1 is a view in perspective of a preferred embodiment of the present invention.

Referring now to the drawings, there is shown Perspectively in FIG. 1 a preferred embodiment 10 of the present invention suitably attached about the circumference of a penis 11. Although apparatus 10 of the present invention may be any suitable structure releasably engagable with penis 11, a preferred embodiment of the present invention is shown as being an adjustable band-like structure 12. Band-like structure 12 is illustrated as being formed from first and second elongated strips of material 13, 14 having first ends 19a, b and second ends 20a, b respectively. First and second elongated strips of material 13, 14 are shown as being overlapped and releasably connected along a portion thereof near first ends 19a, b by a hook-like material 17 and a loop-like material 16. A releasable fastener device 15 is suitably attached to said band-like structure 12 for retaining said second ends 20a, b of said first and second elongated strips of material 13, 14. In addition, suitably attached near second ends 20a, b of first and second elongated strips 13, 14 and further interconnecting elongated strips 13, 14 is an elastic retainer device 18 which prevents the loss of apparatus 10 when fastener 15 releases. Device 18 might be an elongated piece of elastic material.

More particularly, hook-like material 17 is positioned on the side of second elongated strip 14 removed from penis 11 and loop-like material 16 is positioned on the side of first elongated strip 13 adjacent penis 11. First and second elongated strips 13, 14 are overlapped at first ends 19a, b such that hook-like material 16 and loop-like material 17 make contact with each other. Upon making contact hook-like material 16 and loop-like material 17 operatively interact and cooperate with each other to provide a releasable self-gripping, fastening mechanism or material for releasably connecting near first ends 19a, b first and second elongated strips 13, 14. Hook-like material 16 and loop-like material 17 may be any appropriate material such as Velcro (a registered trademark of the Talon Company), which is readily attached and detached but which offers substantial resistance to linear shear forces substantially tangential to the circumference of band-like structure 12.

Figure 2:
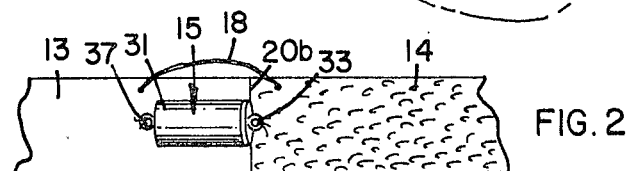
FIG. 2 is a top plan view of a fastener device in a locked state.
Figure 3:
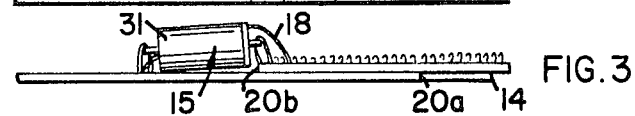
FIG. 3 is a side elevation view of the fastener device in a locked state.
Figure 4:
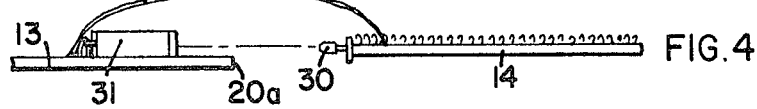
FIG. 4 is a side elevational view of a fastener device in a released state.

First and second elongated strips 13, 14 are releasably interconnected at second ends 20a, b by fastener 15. Fastener 15 may be any suitable fastener mechanism. As illustrated in FIGS. 2 through 4, releasable fastener 15 is a snap-like linear coupling device that includes a penetrator portion 30 and a receptacle portion 31. Penetrator 30 is constructed and arranged so as to be releasably inserted in receptacle 31. Fastener 15 is illustrated in FIGS. 3 and 4 as having two states of operation, the lock or closed position in which penetrator 30 is inserted in receptacle 31 and the unlocked or open position in which penetrator 30 is removed or released from receptacle 31.

Penetrator 30 as illustrated in FIGS. 7 and 2 has a base or collar portion 32 suitably connected to a ring-like structure 33 near second end 20b of second elongated strip 14. As illustrated in FIGS. 2 through 4, ring-like structure 33 is suitably attached to the surface of band-like structure 12 by any suitable method. This might include sewing ring-like structure 33 onto the surface of band-like structure 12. Penetrator portion 30 further includes a narrow intermediate stemlike portion 34 interconnecting base portion 32 with an enlarged head portion 35. Receptacle 31 may be a hollow rigid cylinder 36 open at one end thereof. Cylinder 36 is suitably attached to a ring-like structure 37 which in turn is suitably attached to the surface of band-like structure 12 near second end 20a of first elongated strip 13. Cylinder 36 has a flexible inner liner 38 having a collar portion adjacent the opening into cylinder 36. Collar portion 39 forms a reduced aperture or opening leading into cylinder 36. Inner liner 38 and collar portion 39 may be made of any suitable flexible material such as neoprene.

When a generally linear force, which has a tendency to separate or pull apart penetrator 30 and receptacle 31, is applied to penetrator 30 and receptacle 31, fastener 15 will remain in a locked condition until a predetermined force is applied, at which time fastener 15 will unlock. The predetermined force is determined and preset before use by adjusting the flex characteristics of collar portion 39. Fastener 15 can be adjusted to unlock within a very narrow range of predetermined force.

At second ends 20a, b of elongated strips 13, 14 hook-like material 16 and loop-like material 17 do not make contact and thus do not form a self-gripping connection near ends 20a, b. Fastener 15 while in a locked configuration is the only structure restraining second ends 20a, b such that the configuration of band-like structure 12 is maintained. Thus, all force tangential to the surface of band-like structure 12 about the circumference thereof is applied to fastener 15 and thus detected by fastener 15.

It should be noted that although the structure of fastener 15 has been described in some detail, any suitable releasable fastener may be utilized with the present invention, e.g. a frictional type attachment method might be utilized wherein upon the application of sufficient force the elongated strips which are overlapped near the ends thereof simply slide apart, etc. In addition, although hook-like material 16 and loop-like material 17 have been described, any suitable method for forming band-like structure 12 may be utilized. Indeed, apparatus 10 may have any suitable structure or configuration which is capable of detecting a predetermined radial pressure of penis 11 which is indicative of the hardness or rigidity of penis 11 during a penile tumescent event.

Figure 5:
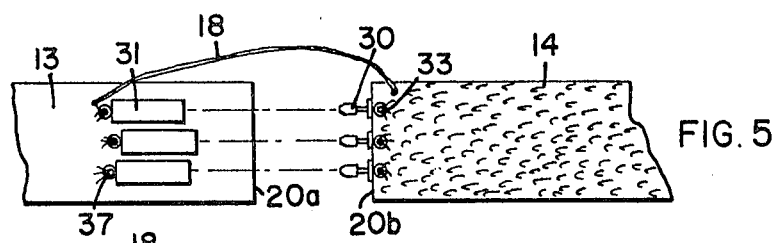
FIG. 5 is a fragmentary top plan view of the present invention having multiple fastener devices shown in a released state.
Figure 6:
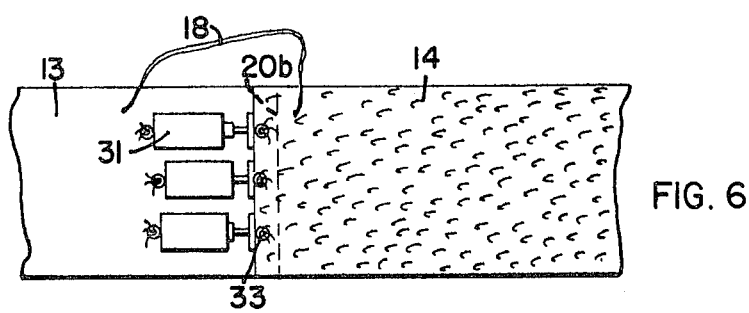
FIG. 6 is a fragmentary top plan view of the present invention having multiple fastener devices in various stages of engagement.

In one embodiment multiple fasteners 15 may be utilized. As illustrated in FIGS. 5 and 6 the receptacle portions 31 of one preferred embodiment are staggered longitudinally along the surface of band-like structure 12 while the penetrator portions 30 are aligned transversely along the surface of band-like structure 12. At any given time only one of fasteners 15 is resisting or opposing the linear force being applied due to the penile tumescent event. Each of the multiple fasteners 15 may be preset to release at differing predetermined forces. Thus fasteners 15 will release at a plurality of different specific force levels during a penile tumescent event yielding a more reliable screening test as to the level of penile rigidity or hardness achieved. The capability to detect a range of release forces, in addition to enabling detection of the absence or presence of a penile tumescent event, enables a more thorough evaluation of the adequacy of penile hardness or rigidity for vaginal penetration.

Illustrated in FIG. 8 is yet another embodiment of a structure for forming an adjustable band-like structure 12. Apertures 50 are defined in a first elongated strip 56 of material. Projections 51 suitably constructed and arranged for releasable insertion into said apertures 50 are positioned on a second elongated strip 57. Projections 51 are inserted into apertures 50 so as to form a releasable connection which offers substantial resistance to linear shear forces. Fastener 15 is suitably attached to elongated strips 56 and 57.

FIGS. 9 and 10 illustrate a further embodiment of band-like structure 12 including two elongated portions of foam-like material 52. Elongated portions 52 may have a loop-like material 53 about the circumference or a portion thereof. Elongated portions 52 may also be made of a foam-like material with a loop-like surface or texture. Elongated foam portions 52 are then releasably interconnected by a piece of material 54 having a hook-like surface 55 as shown in FIG. 9 where the end of material 54 is folded back to reveal hook-like surface 55. Fastener 15 is suitably embedded in the ends of foam-like material portions 52.

It should be noted that the present invention may utilize a detection mechanism connected to suitable recording instruments capable of providing a continuous analog or digital recording of the forces detected during a penile tumescent event, whereby penile hardness or rigidity can be continuously monitored and recorded for sequential penile tumescent events. Such detection devices might, for example, change impedence as the level of the force changes thereby generating responsive signals indicative of penile hardness or rigidity which can be amplified and transmitted through a suitable recording device.

In use, the present invention is sent home with the patient or subject for use at night while sleeping. The patient places band-like structure 12 about the circumference of penis 11 such that the band-like structure fits snug and will not easily slip off. The present invention is constructed and arranged so as to be flexible and adaptable such that band-like structure 12 may be applied while penis 11 is in a flaccid state which is normally the state of penis 11 when apparatus 10 is applied. Penetrator 30 of fastener 15 is inserted into receptacle 31. The opposite ends 19a, b of band-like structure 12 are then overlapped and lightly pressed together such that band-like structure 12 fits snuggly onto penis 11. The light pressing of the ends together enables hook-like material 16 and loop-like material 17 to make contact thereby forming a releasable self-gripping attachment. The patient or subject then goes to sleep and in the morning observes whether fastener 15 is in an open or closed state, thereby indicating whether a predetermined level of penile rigidity or hardness was detected during a penile tumescent event.

Yet another embodiment of the present invention is illustrated in FIGS. 11 through 15. An adjustable band-like structure 62 is illustrated as being formed from first and second elongated strips of flexible material 64, 66 having first ends 64a, 66a and second ends 64b, 66b respectively. The first and second elongated strips are of a predetermined width and are illustrated in FIG. 11 as overlapping one another along a portion thereof near the first and second ends when placed around the shaft of the penis. Furthermore, the first and second elongated strips are releasably interconnected along a portion thereof by a hook-like material 68 and a loop-like material 70. A releasable fastener apparatus 72 is suitably attached to the band-like structure 62 for interconnecting the second ends 64b, 66b of the first and second elongated strips of material 64, 66.

More particularly, the loop-like material 70 is positioned on the surface, of the first and second elongated strips of material, which faces and lies adjacent to the penis 11. Hook-like material 68 is position along a portion of the first elongated strip of material 64 near the first end 64a thereof. Hook-like material 68 is located on the surface facing away from the penis such that when the first and second elongated strips 64, 66 are overlapped, the hook-like and loop-like material make contact with each other. Upon engaging, hook-like material 68 and loop-like material 70 cooperate with each other to provide a releasable, self-gripping attachment or connection. As previously mentioned, the hook-like and loop-like material might be any suitable material, e.g. Velcro (a registered trademark of the Talon Company), which is readily attached and detached but which offers substantial resistance to linear forces substantially tangential to the circumference of the band-like structure 62.

First and second elongated strips 64, 66 are releasably interconnected at the second ends by fastener apparatus 72. As illustrated in FIG. 15, fastener apparatus includes three planer, rectangular strips of material 74, 76 and 78 each having a narrowed weakened portion 74a, 76a and 78a respectively near the center thereof. Each of the strips in the embodiment shown, is adhesively attached to the strip immediately adjacent thereof so as to be fixably secured or attached to each other. In addition, the bottom strip 74 is attached to the outwardly facing surface of the first and second elongated strips thereby effectively attaching all of the strips to the band-like structure. Note, the strips might also be secured to each other by other suitable methods such as heat sealing.

Each of the strips 74 through 78 is uniformly notched along a portion of each side thereof so as to be of lesser transverse extent near the center thereof than at the ends thereof. Consequently, upon the application of sufficient force, the strips 74, 76 and 78 will break near the center thereof.

In the embodiment illustrated, strips 74 through 78 are preferably made of a clear plastic material. The strips 74 and 76 each have a different color marking 82 extending along the longitudinal extent thereof such that each of the strips is readily identified. It will be appreciated that the strips may be made from other suitable material such as metal, etc.

As further illustrated in FIGS. 13 and 15 the strips 74 through 78 are of varying lengths with the lengths thereof increasing from the bottom strip 74 which is the shortest to the top strip 78 which is the longest. Therefore, as illustrated in FIGS. 13 and 14, at any given time only one of the strips is in tension and opposing the force being applied on the band-like structure 62 due to the penile tumescent event. The remainder of the strips are looped upward and not subjected to any force.

As illustrated in FIG. 14, when one of the strips breaks, the second ends 64b, 66b of the first and second strips 64, 66 move in a longitudinal direction relative to each other such that the next adjacent strip is subjected to the force exerted by the penis in the tumescent event.

Consequently, strips 74 through 78 each will break upon the application of a different predetermined force level thereby enabling a range of forces to be detected. Furthermore, the weakened portion of the strips 74, 76 and 78 are strong enough such that none of the strips will break when there is insignificant nocturnal activity, however, all of them will break at their weakened portion when adequate rididity for intercourse is obtained.

When all the strips 74 through 78 are broken due to a penile tumescent event, the band-like structure is no longer connected at the second ends 64b, 66b thereby enabling the band-like structure to fall from the penis so as to assure the patient is not injured.

It will be appreciated that the above described embodiment is intended for a single use. This insures increased reliability as the environment of the penile rigidity measuring apparatus may be carefully controlled by sealing the device in suitable packaging until the time of use. Once used, the apparatus may be disposed of such that for every testing occasion a new apparatus may be used.

In addition, the plastic snap elements or strips 74 through 78 are not affected by environmental conditions to the extent that the stamps utilized in the stamp testing method are affected. Whereas the stamps might break upon application of force having a magnitude anywhere from roughly from 15 to 40 ounces, the plastic strips of the present invention have a sensitivity or accuracy of plus or minus 10 percent of their preestablished value. The applicant has found that utilizing three plastic snap elements or strips which will break upon the application of 9 ounces, 15 ounces, and 20 ounces of force respectively, provides for effective penile tumescent monitoring. It will be appreciated however, that one or any number of plastic strips might be utilized for testing purposes.

In the preferred embodiment, all three of the plastic strips have a different thickness. In addition, while the top two strips 78 and 76 have the same tensile strength, the bottom strip 74 has a different tensile strength. It will be appreciated, that varying combinations of strip configurations and tensile strengths might be utilized in keeping with the principles of the present invention.

The present invention thus provides a reliable and easy to use apparatus for nocturnal monitoring of penile rigidity or hardness. The fasteners can be made to release consistently and accurately within a narrow range of force levels. The present invention is easy to use and reliable in that it requires that the patient merely press together the ends of the elongated strips of material so as to form a band-like structure which fits snugly onto varying sizes of penises. The self-gripping material of the present invention provides substantial resistance to linear shear forces about the circumference of band-like structure but is easily activated by merely pressing the material lightly together or separated by pulling apart. In addition, the present invention can easily be attached should it become accidentally dislodged during placement on penis 11.

The present invention also enables the detection of multiple levels of force during a penile tumescent event. This enables the presence or absence of significant penile tumescent activity to be detected and if present, the adequacy of penile hardness or rigidity for vaginal penetration to be more accurately assessed.

Significant also is that the present invention allows screening or testing of individuals in a safe and effective manner for psychogenic or organic impotence while the individuals are at home. This will enable and encourage more individuals to utilize this screening technique as the screening can be inexpensively and readily performed.

It should be understood that even though the numerous characteristics and advantages of the invention have been set forth in the foregoing description, together with details of the structure and function of the invention, the disclosure is illustrative only, and changes may be made in detail, especially in matters of shape, size and arrangement of parts within the principle of the invention, to the full extent indicated by the broad general meaning of the terms in which the appended claims are expressed.

What is claimed is:

1. An apparatus for measuring penile rigidity in a penile tumescent event, comprising:
   (a) first and second elongated flexible strips of material having first and second ends and inner and outer surfaces,
   (b) a single elongated flexible element interconnecting said first and second elongated flexible strips proximate said second ends, said flexible element having a notch intermediate the ends thereof defining a weakened portion having a predetermined tensile strength substantially less than the strength of said strips, and
   (c) means for releasably and adjustably attaching the first ends of said flexible strips together so as to enable a band of adjustable circumference to be formed around the penis so that said weakened portion can break apart to indicate a tumescent event having predetermined penile rigidity.

2. An apparatus for measuring penile rigidity in a penile tumescent event, comprising:
   (a) first and second elongated flexible members each having first and second ends and inner and outer surfaces;
   (b) a plurality of elongated flexible elements attached to and connecting the second ends of said first and second elongated flexible members, each element having a weakened portion having a predetermined tensile strength substantially less than the strength of said flexible members, said elongated flexible elements being configured and attached to said first and second elongated members such that at various relative displacements between said second ends of said first and second elongated flexible members, less than all of said elongated flexible elements are in tension; and
   (c) means for releasably and adjustably attaching the first ends of said flexible members together so as to enable a band of adjustable circumference to be formed around the penis with less than all elements in tension at any one time.

3. The apparatus of claim 2 wherein said elongated flexible elements are plastic.

4. The apparatus of claim 2 wherein said elongated flexible elements have different lengths between points of attachment between said first and second elongated flexible members.

5. The apparatus of claim 2 wherein said weakened portions are defined by a notch formed on said flexible elements.

6. The apparatus of claim 2 wherein each said elongated flexible element has a different color code so as to be easily identified.

* * * * *

UNITED STATES PATENT AND TRADEMARK OFFICE
CERTIFICATE OF CORRECTION

PATENT NO. : 4,474,187          Page 1 of 2

DATED : October 2, 1984

INVENTOR(S) : Gerald W. Timm et al.

It is certified that error appears in the above—identified patent and that said Letters Patent is hereby corrected as shown below:

In Column 2, line 68 to Column 3, line 2, delete "releasable self-gripping fastening material such as Velcro. (Velcro is a registered trademark of the Talon Company.)" and insert --releasable self-gripping fastening material such as Velcro brand fasteners. (Velcro is a registered trademark of Velcro USA Inc., 406 Brown Avenue, Manchester, New Hampshire.)--.

In Column 8, lines 25-26, delete "material, e.g. Velcro (a registered trademark of the Talon Company)," and insert --material, e.g. Velcro brand fasteners (a registered trademark of Velcro USA Inc.),--.

UNITED STATES PATENT AND TRADEMARK OFFICE
CERTIFICATE OF CORRECTION

PATENT NO. : 4,474,187           Page 2 of 2

DATED      : October 2, 1984

INVENTOR(S) : Gerald W. Timm et al.

It is certified that error appears in the above-identified patent and that said Letters Patent is hereby corrected as shown below:

Column 4, line 38

"perferred" should be --preferred--

Column 5, lines 16-17

"Perspectively" should be --perspectively--

Column 8, line 14

"position" should be --positioned--

Column 8, line 33

"planer" should be --planar--

Column 9, line 10

"rididity" should be --rigidity--

Signed and Sealed this

Sixteenth Day of April 1985

[SEAL]

Attest:

DONALD J. QUIGG

*Attesting Officer*     *Acting Commissioner of Patents and Trademarks*